United States Patent
Sakuma et al.

(10) Patent No.: US 11,197,773 B2
(45) Date of Patent: Dec. 14, 2021

(54) INTRAORAL DEVICE CONTROL SYSTEM

(71) Applicant: International Business Machines Corporation, Armonk, NY (US)

(72) Inventors: Katsuyuki Sakuma, Fishkill, NY (US); Stephen John Heisig, Tarrytown, NY (US); Michael Angelo Stellitano, Newburgh, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/817,167

(22) Filed: Mar. 12, 2020

(65) Prior Publication Data
US 2021/0282953 A1    Sep. 16, 2021

(51) Int. Cl.
*A61F 4/00* (2006.01)
*G06F 3/01* (2006.01)
(Continued)

(52) U.S. Cl.
CPC .............. *A61F 4/00* (2013.01); *G06F 3/011* (2013.01); *G06F 3/0338* (2013.01); *A61C 7/08* (2013.01); *H03F 3/45* (2013.01)

(58) Field of Classification Search
CPC .. A61C 7/002; A61C 7/08; H04B 5/00; H04B 5/0081; H04B 5/0056;
(Continued)

(56) References Cited

U.S. PATENT DOCUMENTS 6,089,864 A    7/2000  Buckner et al.
6,280,394 B1 *  8/2001  Maloney ............ A61B 5/04888
                                                        600/546
(Continued)

FOREIGN PATENT DOCUMENTS

CN    110007767 A    7/2019
EP    2537492 A1    12/2012
(Continued)

OTHER PUBLICATIONS

"Ecoflex 00-50", "Ecoflex™ 00-50", Smooth-On, https://www.smooth-on.com/products/ecoflex-00-50/, Accessed on Sep. 11, 2019, 10 pages.

(Continued)

*Primary Examiner* — Kenneth Bukowski
(74) *Attorney, Agent, or Firm* — Stephen R. Tkacs; Stephen J. Walder, Jr.; Kristofer L. Haggerty (57) ABSTRACT

Mechanisms are provided to implement an intraoral control mechanism that allows a user to control an operation of a computer system or an electronic device. The intraoral control mechanism detects a strain based on a tongue of a user moving a control mechanism away from a fixed position; transduces the detected strain into a control signal; amplifies an amplitude of the control signal thereby producing an amplified control signal; converts the amplified control signal to a digital input signal; modulates the digital input signal onto a transmission frequency wave; and transmits the digital input signal to the computer system. The computer system may then either execute the digital control signal on the computer system itself to perform an operation or transmit the digital control signal to the electronic device so as to operate as indicated by the digital control signal. The digital input signal is saved for characterization of the user.

20 Claims, 7 Drawing Sheets

(51) Int. Cl.
  *G06F 3/0338* (2013.01)
  *A61C 7/08* (2006.01)
  *H03F 3/45* (2006.01)

(58) Field of Classification Search
  CPC ... H04B 5/0031; A61B 5/0015; A61B 5/0488; A61B 5/0816; A61B 5/4818; A61B 5/682; H04Q 9/00; H04Q 2209/43; H04Q 2209/50
  See application file for complete search history.

(56) References Cited

U.S. PATENT DOCUMENTS

| | | | |
|---|---|---|---|
| 2005/0113654 A1 | 5/2005 | Weber et al. | |
| 2005/0275620 A1* | 12/2005 | Manal | G06F 3/04817 345/156 |
| 2015/0301619 A1 | 10/2015 | Menon et al. | |
| 2016/1544681 | 6/2016 | Kimmel | |
| 2016/0250054 A1 | 9/2016 | Al-Tawil et al. | |
| 2017/0087363 A1* | 3/2017 | Costanzo | G16H 20/10 |
| 2018/0000563 A1* | 1/2018 | Shanjani | A61B 5/4818 |
| 2018/0085061 A1 | 3/2018 | Heisig et al. | |
| 2018/0116594 A1 | 5/2018 | Heisig et al. | |
| 2019/0004596 A1 | 1/2019 | Henrique Barbosa Postal et al. | |

FOREIGN PATENT DOCUMENTS

| | | |
|---|---|---|
| JP | 2004329954 A | 11/2004 |
| JP | 2005215818 A | 11/2005 |

OTHER PUBLICATIONS

Houghton1, Todd et al., "Stretchable Capacitive Strain Sensors Based on a Novel Polymer Composite Blend", 2017 IEEE 67th Electronic Components and Technology Conference, May 30-Jun. 6, 2017, 6 pages.

Israel, Brett, "Tongue Drive Wheelchair", https://www.news.gatech.edu/features/tongue-drive-wheelchair, Accessed Sep. 11, 2019, 3 pages.

Svane-Knudsen, Ditte, "The tongue is the future for disabled people", https://sciencenordic.com/denmark-disability-diseases/the-tongue-is-the-future-for-disabled-people/1372887, Published Jun. 7, 2012, 10 pages.

Velasquez-Lopez, Alejandro et al., "Development of a Tongue Machine Interface for Quadriplegic Patients", 21st International Conference on Engineering Design, ICED 17, Aug. 21-25, 2017, 10 pages.

Zeiser, Roderich et al., "Capacitive strain gauges on flexible polymer substrates for wireless, intelligent systems", Journal of Sensors and Sensor Systems, vol. 1 Issue 3, 2014, 10 pages.

International Search Report and Written Opinion dated May 26, 2021 for International Application No. PCT/IB2021/051816, 9 pages.

* cited by examiner

INTRAORAL DEVICE CONTROL SYSTEM

BACKGROUND

The present application relates to an intraoral device and user interface system for controlling a computer or other device by movement of the user's tongue and jaw. It can be used by people with different needs for assistance, i.e. from no physical disability all the way up to quadriplegia. The mechanisms may be used by people in tasks where both hands and possibly feet are occupied or in cases where they do not have the use of their hands or feet. The mechanisms may also be used in situations where it is not advisable to look away from the current task and the user needs to make a control input to a computer system or device.

Assistive devices are non-medical tools which relate to and assist with mobility, transportation, communication, activities of daily living, and performance of job related activities. The most common examples of assistive devices are mobility devices such as wheelchairs, walkers, and crutches that help people who are unable to walk on their own. Adaptive technology is a type of assistive technology where existing tools are adapted for use by individuals with disabilities. These assistive devices may be used not just by people with 'traditional' mobility impairments, but also by people with cardiovascular, fatigue-based, paralysis-based, or the like, conditions.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method, in a data processing system, is provided for implementing an intraoral control mechanism that allows a user to control an operation of a computer system or an electronic device in accordance with an illustrative embodiment. The illustrative embodiment detects, by a sensor of the intraoral control mechanism, a strain based on a tongue of a user moving a control mechanism away from a fixed position. The illustrative embodiment transduces, by the sensor, the detected strain into a control signal. The illustrative embodiment amplifies, by an amplifier of the intraoral control mechanism, an amplitude of the control signal thereby producing an amplified control signal. The illustrative embodiment converts, by an analog-to-digital converter of the intraoral control mechanism, the amplified control signal to a digital input signal. The illustrative embodiment modulates, by a radio frequency (RF) microcontroller of the intraoral control mechanism, the digital input signal onto a transmission frequency wave. The illustrative embodiment transmits, by the RF microcontroller, the digital input signal to the computer system which then interprets the digital input signal by means of pre-trained classifiers and other software into a digital control signal. The illustrative embodiment then either executes the digital control signal on the computer system itself and performing a operation associated with the digital control signal or transmits the digital control signal to an electronic device control mechanism of the electronic device thereby causing the electronic device in which the electronic device control mechanism is comprised to operate as indicated by the digital control signal. The illustrative embodiment may also save the digital input signal for characterization of the user's health state.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Accessibility-limited users, such as amputees, paralysis-based users, including hemiplegic, monoplegic, paraplegic, quadriplegic, or the like, as well as other users who are not affected with such conditions utilize devices to provide input to a data processing system which may in turn control other devices or systems. These devices and systems may include surgical robots, flight or other vehicle control systems, phones, lights, air conditioning and heating systems, shades, wheelchairs, or other mobility devices. Controllable systems also include immersive augmented reality (AR) and virtual reality (VR) technologies (e.g. Microsoft Hololens, Google Glass, etc.). Head-mounted technology worn in daily life is difficult to control when hands are being used for driving, surgery, walking, or other concurrent tasks. With regard to wheelchairs, previous examples of such control systems may be the 'sip and puff' type mouth-controlled wheelchair systems, the lip-controlled joystick wheelchair system, the tongue implant controlled wheelchair system, or the like. However, the 'sip and puff' type mouth-controlled wheelchair system is not a haptically intuitive way to control motion. Additionally, the lip-controlled joystick wheelchair system is complicated, bulky, and requires adjustment by other people. Further, the tongue controlled wheelchair systems require a tongue implant so as to either detect changes in magnetic fields or implement the required tapping on a set of contacts. Further implementations of control systems include non-keyboard based communication tools that utilize input from pointing sticks and eye trackers. These non-keyboard based communication tools require dedicated applications, meaning it is difficult to do anything else and requires a large amount of dexterity (using neck muscles to turn the whole head) and concentration.

The illustrative embodiments describe a soft, biologically inspired, eccentrically shaped 'controller' that may be constructed in shapes that are easily manipulated with a body part (e.g. tongue) but otherwise stay out of the way during other uses (e.g. chewing, swallowing, talking). The movements of this controller by the human user is transduced by one or more strain gauges, pressure sensors, or other sensors, into a digital input signal that is transmitted to a computer system which could be a smart watch, phone, laptop, or other such device. There it is deconvolved by trained classifiers running on a computer system into 'control' operations, such as on, off, select, forward, backward, left, right, up, down, or any other arbitrary command. These control commands may then affect the receiving computer system or be passed on to another system or a controlled device. Input signals from the device generated during the course of daily life may also be used to characterize activities and health states related to chewing, swallowing, coughing, bruxism, temporomandibular joint disorders. The signal is deconvolved in a similar way to control commands with different features being generated.

Before beginning the discussion of the various aspects of the illustrative embodiments and the improved computer operations performed by the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on hardware to thereby configure the hardware to implement the specialized functionality of the present invention which the hardware would not otherwise be able to perform, software instructions stored on a medium such that the instructions are readily executable by hardware to thereby specifically configure the hardware to perform the recited functionality and specific computer operations described herein, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

Figure 1:
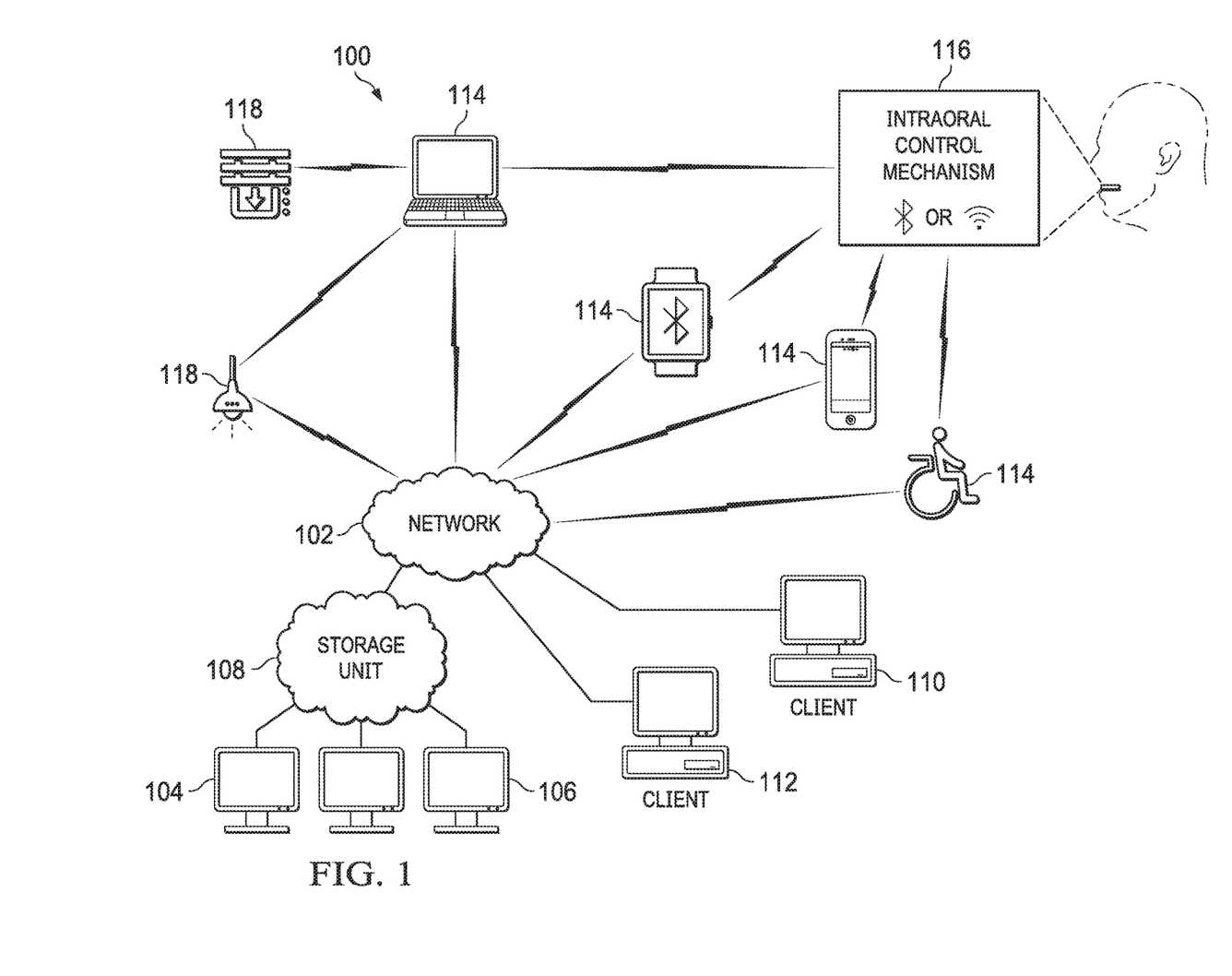
FIG. 1 is an example diagram of a distributed data processing system in which aspects of the illustrative embodiments may be implemented.
Figure 2:
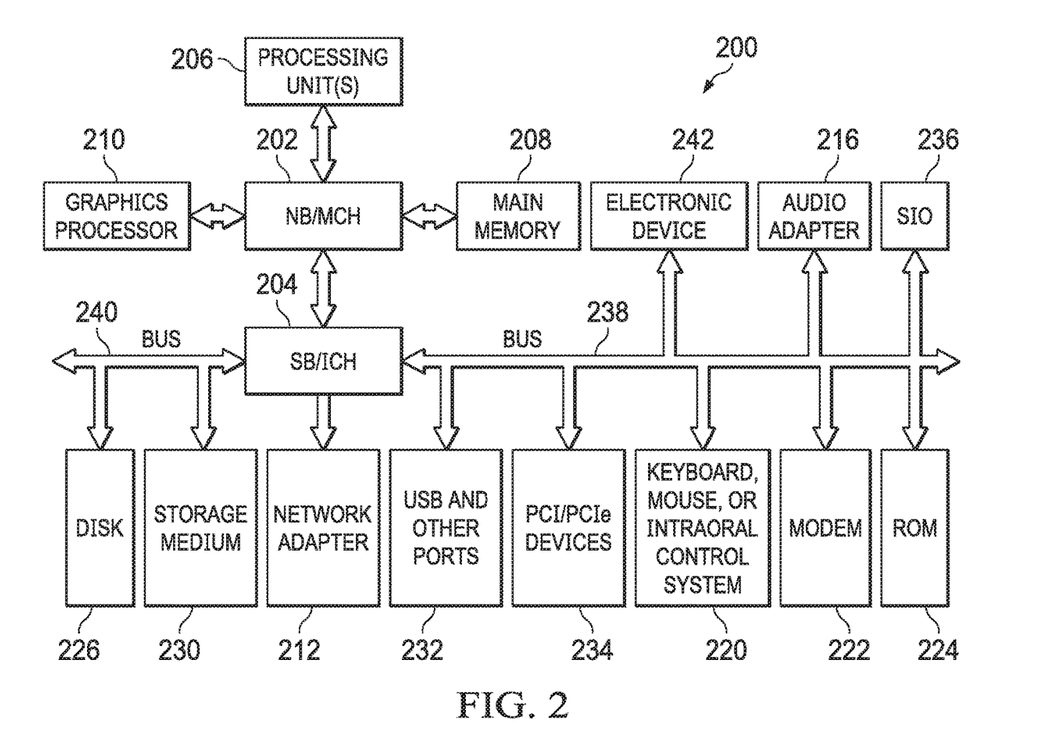
FIG. 2 is an example block diagram of a computing device in which aspects of the illustrative embodiments may be implemented.

Thus, the illustrative embodiments may be utilized in many different types of data processing environments. In order to provide a context for the description of the specific elements and functionality of the illustrative embodiments, FIGS. 1 and 2 are provided hereafter as example environments in which aspects of the illustrative embodiments may be implemented. It should be appreciated that FIGS. 1 and 2 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example distributed data processing system in which aspects of the illustrative embodiments may be implemented. Distributed data processing system 100 may include a network of computers in which aspects of the illustrative embodiments may be implemented. The distributed data processing system 100 contains at least one network 102, which is the medium used to provide communication links between various devices and computers connected together within distributed data processing system 100. The network 102 may include connections, such as wire, wireless communication links, or fiber optic cables.

In the depicted example, intraoral control mechanism 116 communicates with any of a set of devices 114 such as a phone, watch, laptop, home hub server, wheelchair, or the like, via different wireless protocols such as Bluetooth, Zigbee, NFC, Wi-Fi, LiFi, 3G, etc., that can operate to some extent interactively and autonomously. The set of devices 114 receive input from intraoral control mechanism 116 and translate the input into commands or communication primitives by means of software typically using machine learning models. These communication requests may be turned into character input, and cursor movement for email or other computer function, wheelchair directions, health metrics related to talking, chewing, swallowing, coughing, etc. These communications may operate on one or more of the set of devices 114 or be stored or forwarded. Other devices 118 with their own protocols, which may be connected through wired network or through different wireless protocols such as Bluetooth, Zigbee, NFC, Wi-Fi, LiFi, 3G, etc., that can operate to some extent interactively and autonomously, may be controlled or influenced by one or more of the set of devices 114 based on input from intraoral control mechanism 116. In one example, home lighting and shades are controlled by a home hub device connected to intraoral control mechanism 116. In the depicted example, a set of devices server 104 and server 106 are connected to network 102 along with cloud-based analytics and storage 108. In addition, clients 110 and 112, and smart device 114 are also connected to network 102. In the depicted example, server 104 provides data, such as boot files, operating system images, and applications to the clients 110 and 112 and smart device 114. Clients 110 and 112 are clients to server 104 in the depicted example. Clients 110 and 112 may be, for example, personal computers, network computers, or the like. Distributed data processing system 100 may include additional servers, clients, and other devices not shown. Cloud-based analytics and storage 108 is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. Thus, a cloud computing environment is service oriented with a focus on statelessness, low coupling, modularity, and semantic interoperability. At the heart of cloud computing is an infrastructure comprising a network of interconnected nodes.

In the depicted example, distributed data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 100 may also be implemented to include a number of different types of networks, such as for example, an intranet, a local area network (LAN), a wide area network (WAN), body area network, Wi-Fi, Bluetooth, Bluetooth low energy, near-field communication (NFC), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

As shown in FIG. 1, one or more of the computing devices, e.g., 114 and server 104, may be specifically configured to implement a control mechanism for providing input to a computing device or controlling the operation of an electronic device. The configuring of the computing device may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 104, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general purpose computing device. Moreover, as described hereafter, the implementation of the mechanisms of the illustrative embodiments improves the functionality of the computing device and provides a useful and concrete result that facilitates providing input to a computing device or controlling an operation of an electronic device utilizing an intraoral control mechanism.

As noted above, the mechanisms of the illustrative embodiments utilize specifically configured computing devices, or data processing systems, to perform the operations for providing input to a computing device or controlling an operation of an electronic device utilizing an intraoral control mechanism. These computing devices, or data processing systems, may comprise various hardware elements which are specifically configured, either through hardware configuration, software configuration, or a combination of hardware and software configuration, to implement one or more of the systems/subsystems described herein. FIG. 2 is a block diagram of just one example data processing system in which aspects of the illustrative embodiments may be implemented. Data processing system 200 is an example of a computer, such as server 104 in FIG. 1, in which computer usable code or instructions implementing the processes and aspects of the illustrative embodiments of the present invention may be located and/or executed so as to achieve the operation, output, and external effects of the illustrative embodiments as described herein.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP).

In the depicted example, local area network (LAN) adapter 212 connects to SB/ICH 204. Audio adapter 216, user interface 220, which may be a keyboard, mouse adapter, or intraoral control system 220, modem 222, read only memory (ROM) 224, hard disk drive (HDD) 226, storage medium 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and storage medium 230 connect to SB/ICH 204 through bus 240. HDD 226 and storage medium 230 may use, for example, an integrated drive electronics (IDE) or serial advanced technology attachment (SATA) interface. Super I/O (SIO) device 236 may be connected to SB/ICH 204.

An operating system runs on processing unit 206. The operating system coordinates and provides control of various components within the data processing system 200 in FIG. 2. As a client, the operating system may be a commercially available operating system such as Microsoft® Windows 10®, Swift®, Python®, or the like. An object-oriented programming system, such as the Java™ programming system, may run in conjunction with the operating system and provides calls to the operating system from Java™ programs or applications executing on data processing system 200.

As a server, data processing system 200 may be, for example, any general purpose computer system, running any general purpose operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. The processes for illustrative embodiments of the present invention may be performed by processing unit 206 using computer usable program code, which may be located in a memory such as, for example, main memory 208, ROM 224, or in one or more peripheral devices 226 and 230, for example.

A bus system, such as bus 238 or bus 240 as shown in FIG. 2, may be comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache such as found in NB/MCH 202 in FIG. 2.

As mentioned above, in some illustrative embodiments the mechanisms of the illustrative embodiments may be implemented as application specific hardware, firmware, or the like, application software stored in a storage device, such as HDD 226 and loaded into memory, such as main memory 208, for executed by one or more hardware processors, such as processing unit 206, or the like. As such, the computing device shown in FIG. 2 becomes specifically configured to implement the mechanisms of the illustrative embodiments and specifically configured to perform the operations and generate the outputs described hereafter with regard to the intraoral control mechanism for providing input to data processing system 200 through cursor inputs to data processing system 200 or controlling an operation an electronic device, such as electronic device 242, as will be described hereafter.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Figure 3:
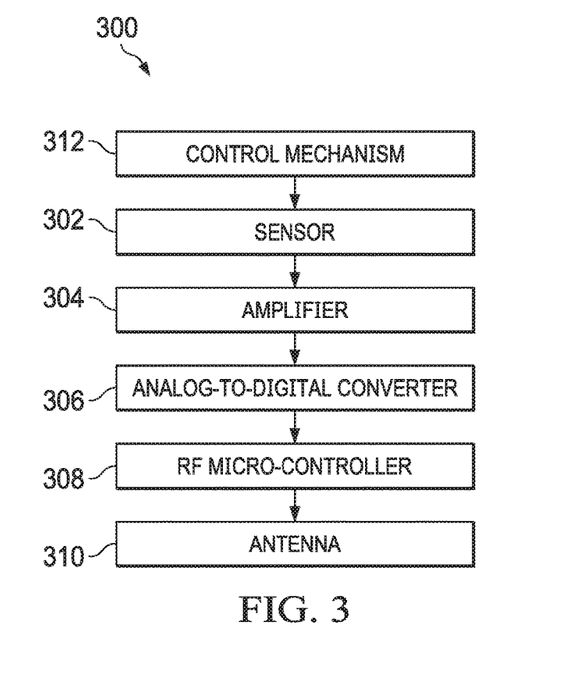
FIG. 3 depicts one exemplary functional block diagram of an intraoral control mechanism for a user to control an operation of an electronic device in accordance with an illustrative embodiment.

FIG. 3 depicts one exemplary functional block diagram of an intraoral control mechanism for a user to control an operation of an electronic device in accordance with an illustrative embodiment. Intraoral control mechanism 300 comprises sensor 302, amplifier 304, analog-to-digital converter 306, radio frequency (rf) microcontroller 308, and antenna 310. Sensor 302 may be one or more sensors such as strain gauge sensor, pressure sensor, or the like, that measure strains, such as stress, force, torque, or other stimuli including displacement, acceleration, or position. Sensor 302 may be structured from metal (foil); semiconductor (referred to as piezo-resistive, where the base material is doped, by diffusion of doping materials (usually boron or arsenide for p or n type) to obtain a base resistance as needed), piezoelectric materials (usually perovskites (PZT)), or the like. In accordance with the illustrative embodiments, sensor 302 is coupled to a control mechanism 312 which may take the form of kinematic, spreading, breakup, recoiling, bouncing, or the like feature which, when touched by the tongue of a user, causes a strain on control mechanism 312 that is sensed by sensor 302. That is, the movement of control mechanism 312 by the tongue of a user is transduced by sensor 302 into a control signal such as on, off, select, forward, backward, left, right, up, down, etc. In accordance with the illustrative embodiments, control mechanism 312 has 360 degrees of motion as well as an up motion followed by a down motion.

Amplifier 304 receives this control signal and uses electric power from a power supply to increase the amplitude of a control signal applied to its input terminals, producing a proportionally greater amplitude control signal at its output terminal. Analog-to-digital converter 306 receives this amplified control signal in the form of an analog signal and converts the analog amplified control signal into a digital input signal. Radio frequency (RF) microcontroller 308 receives the digital input signal and modulates the digital input signal onto a desired transmission frequency wave, such as Wi-Fi, Bluetooth, near-field communication (NFC), body area network, Bluetooth low energy, or the like, that RF microcontroller 308 then transmits out via antenna 310. The digital input signal transmitted by RF microcontroller 308 is then received by a matching network antenna (not shown) which is then utilized by computer system which interprets the digital input signal by means of pre-trained classifiers and other software into a digital control signal, such that the computer system executes the digital control signal on the computer system itself and performs a operation associated with the digital control signal or transmits the digital control signal to an electronic device control mechanism of the electronic device thereby causing the electronic device in which the electronic device control mechanism is comprised to operate an electronic device in an associated manner.

In accordance with one illustrative embodiment, intraoral control mechanism 300 may take the form of a dental retainer that is custom-made and removable. The center section of the dental retainer, i.e. the molded plastic center section that affixes to the hard palate in the user's mouth, comprises at least control mechanism 312 and sensor 302. Amplifier 304, analog-to-digital converter 306, RF microcontroller 308, and antenna 310 may be comprised within the molded plastic center section or affixed to the wires that wrap around the user's upper teeth and hold the dental retainer in the user's mouth.

As user dexterity differs from user to user, a user's use of control mechanism 312 may be used, as one example, to train a wheelchair direction control mechanism. That is, upon initial use, the user performs a particular operation of a set of operations, such as on, off, forward, backward, left, right, up, or the like, using control mechanism 312 repeated times. Thus, as the user performs the particular operation, for example forward, repeatedly using control mechanism 312, the wheelchair direction control mechanism labels the signal received via intraoral control mechanism 300 and associates the received signal with the forward label, thus training wheelchair direction control mechanism. This process is repeated for each of the set of operations. After training, as the user moves the control mechanism 312, the wheelchair direction control mechanism receives a signal from intraoral control mechanism 300 and moves the wheelchair in the direction associated with the trained signaling.

Thus, the illustrative embodiments provide a soft, biologically inspired eccentrically shaped 'controller' that may be constructed in shapes that are easily manipulated with a body part (e.g. tongue) but otherwise stay out of the way during other uses (e.g. chewing, swallowing, talking). The movements of this controller by the human user is transduced by a sensor into a digital signal that is deconvolved by trained classifiers into 'control' operations, such as on, off, select, forward, backward, left, right, up, etc. These control operations include directional, idiomatic, character, or other input type signals.

Figure 4:
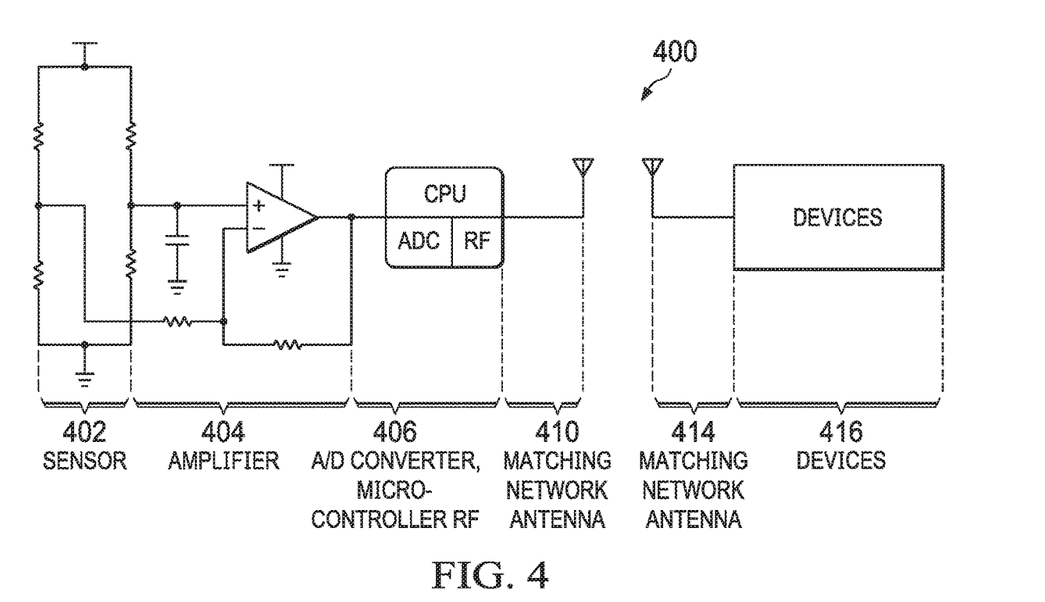
FIG. 4 depicts one example of an electrical circuit schematic of an intraoral control mechanism for a user to control the operation of an electronic device in accordance with an illustrative embodiment.

FIG. 4 depicts one example of an electrical circuit schematic of an intraoral control mechanism, such as intraoral control mechanism 300 of FIG. 3, for a user to control the operation of an electronic device in accordance with an illustrative embodiment. Intraoral control mechanism 400 comprises sensor 402, amplifier 404, analog-to-digital converter/RF microcontroller 406, and matching network antenna 410. Sensor 402, which is similar to sensor 302 of FIG. 3, may be a sensor such as strain gauge sensor, pressure sensor, or the like, that measures strains, such as stress, force, torque, or other stimuli including displacement, acceleration, or position. Sensor 402 is illustrated as a Wheatstone bridge circuit that is an electrical circuit used to measure an unknown electrical resistance by balancing two legs of a bridge circuit, one leg of which includes the unknown component. In this instance, the unknown component is a piezoresistive sensor. In accordance with the illustrative embodiments, sensor 402 is coupled to a control mechanism which may take the form of kinematic, spreading, breakup, recoiling, bouncing, or the like feature, which, when touched by the tongue of a user, causes a strain on the control mechanism that is sensed by sensor 402. That is, the movement of the direction control mechanism by the tongue of a user is transduced by sensor 402 into a directional control signal such as on, off, select, forward, backward, left, right, up, down, etc. While FIG. 4 illustrates only one sensor 402, so as to provide higher accuracies in detecting movement by the user's tongue, a plurality of sensors 402 may be utilized.

Sensor 402, as well as other power consuming devices of FIG. 4, may be powered in many different ways. In one embodiment, power may be provided via a rechargeable coin battery, which may be recharged when intraoral control system is removed from the user's mouth and placed in a charging station or recharged while intraoral control system is still in the user's mouth via a wireless charging system, such as near-field communication (NFC), radio frequency (RF) over-the-air charging, or the like. In another embodiment, power may be provided directly via NFC, RF over-the-air charging, or the like. In yet another embodiment, an energy harvesting circuit may be used as a power supply, such as a piezoelectric circuit, friction circuit, chewing-based circuit, or the like.

Amplifier 404 receives this directional control signal and uses electric power from a power supply to increase the amplitude of a directional control signal applied to its input terminals, producing a proportionally greater amplitude directional control signal at its output terminal. Analog-to-digital converter/RF microcontroller 406 receives this amplified directional control signal in the form of an analog signal and converts the analog amplified directional control signal into a digital directional control signal, which is then modulated onto a desired transmission frequency wave, such as Wi-Fi, Bluetooth, near-field communication (NFC), body area network, Bluetooth low energy, or the like, that is then transmitted out via matching network antenna 410. Matching network antenna 414, which is coupled to device 416, which may be one or more of a set of devices such as set of devices 114, receives the digital directional control signal transmitted by analog-to-digital converter/RF microcontroller 406 that is then utilized by device 416 to operate an associated electronic device in an associated manner.

Figure 5A:
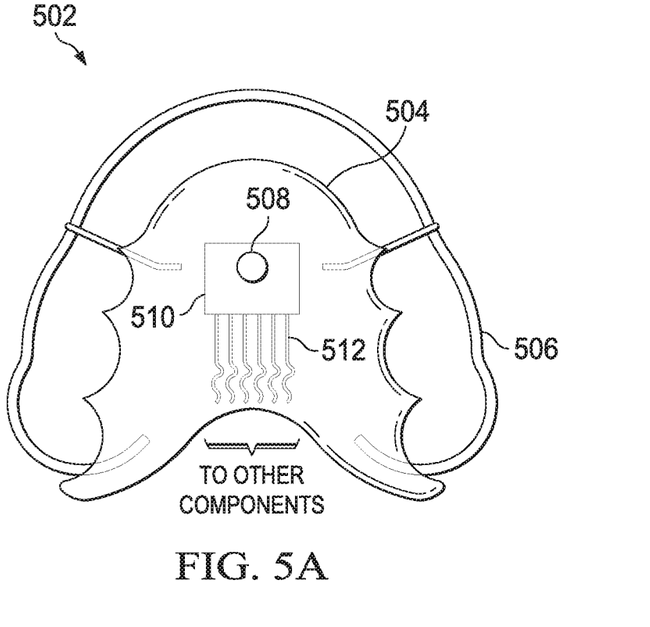
FIGS. 5A-5D depict one implementation, as an example, of an intraoral control mechanism in accordance with an illustrative embodiment.

FIGS. 5A-5D depict one implementation, as an example, of an intraoral control mechanism, such as intraoral control mechanism 300 of FIG. 3 and intraoral control mechanism 400 of FIG. 4, in accordance with an illustrative embodiment. As stated previously, intraoral control mechanism 300/400 may take the form of a dental retainer that is custom-made and removable. FIG. 5A depicts one exemplary dental retainer comprising an intraoral control mechanism in accordance with an illustrative embodiment. Dental retainer 502 is comprised of a molded plastic center section 504 affixed to wires 506 that wrap around the user's upper teeth and hold dental retainer 502 in the user's mouth. Molded plastic center section 504 comprises at least direction control mechanism 508 and sensor 510. Sensor 510 is coupled to other components, i.e. the amplifier, analog-to-digital converter, RF microcontroller, and antenna, which may be comprised within the molded plastic center section 504 or affixed to wires 506, via coupling 512. As a note, sensor 510 may be a plurality of sensors so as to provide higher accuracies in detecting movement by the user's tongue. In FIG. 5A, coupling 512 is shown to have six wires. This is because, in this example, sensor 510 is utilizing three strain gauges and each strain gauge requires two wires. Thus, the six wires are only one example, and sensor 510 may comprise any number of sensors so as to provide higher accuracies in detecting movement by the user's tongue. It should also be noted that all devices, i.e. sensor 510, coupling 512, or the like, are insulated in accordance with the illustrative embodiments so as to protect the user.

Figure 5B:
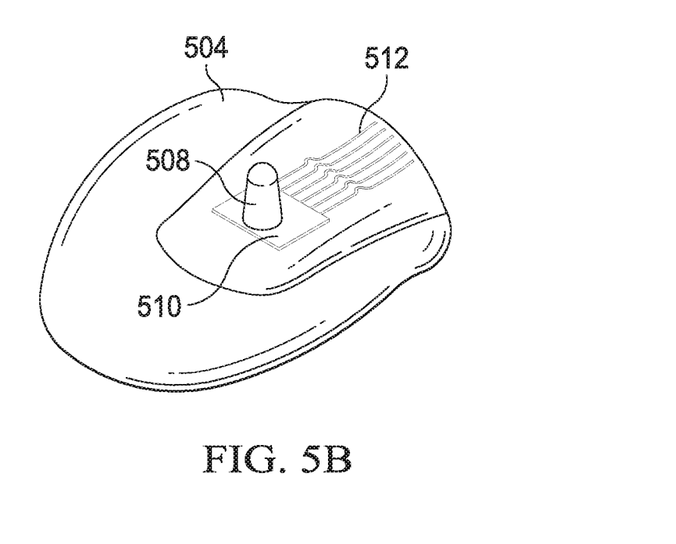

FIG. 5B depicts another view of molded plastic center section 504 in accordance with an illustrative embodiment. As is illustrated, molded plastic center section 504 comprises at least direction control mechanism 508 and sensor 510, which are coupled to other components, i.e. the amplifier, analog-to-digital converter, RF microcontroller, and antenna via coupling 512. Again, the other components, i.e. the amplifier, analog-to-digital converter, RF microcontroller, and antenna, which are coupled to sensor 510 via coupling 512 may be comprised within the molded plastic center section 504 or affixed to the wires that encompass molded plastic center section 504.

Figure 5C:
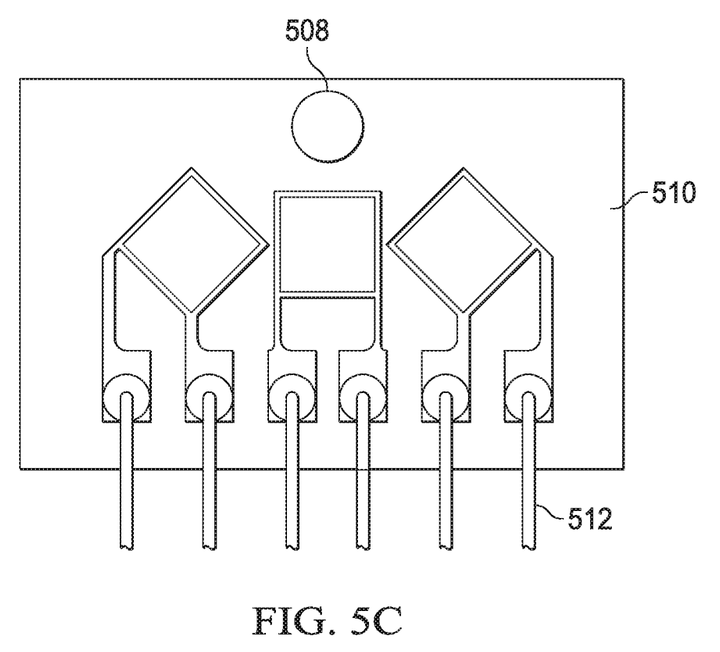

FIG. 5C depicts a magnified view of direction control mechanism 508 and sensor 510 in accordance with an illustrative embodiment. In the depicted example, sensor 510 is illustrated as a foil that includes three strain gauges (piezo-resistive) sensors. Again, while sensor 510 of FIG. 5C illustrates three strain gauges, the illustrative embodiments recognize that any number sensors may be utilized so as to provide higher accuracies in detecting movement by the user's tongue. In FIG. 5C, coupling 512 is shown to have six wires. This is because, in this example, sensor 510 is utilizing three strain gauges and each strain gauge requires two wires. Thus, the six wires are only one example and sensor 510 may comprise any number of sensors so as to provide higher accuracies in detecting movement by the user's tongue.

Figure 5D:
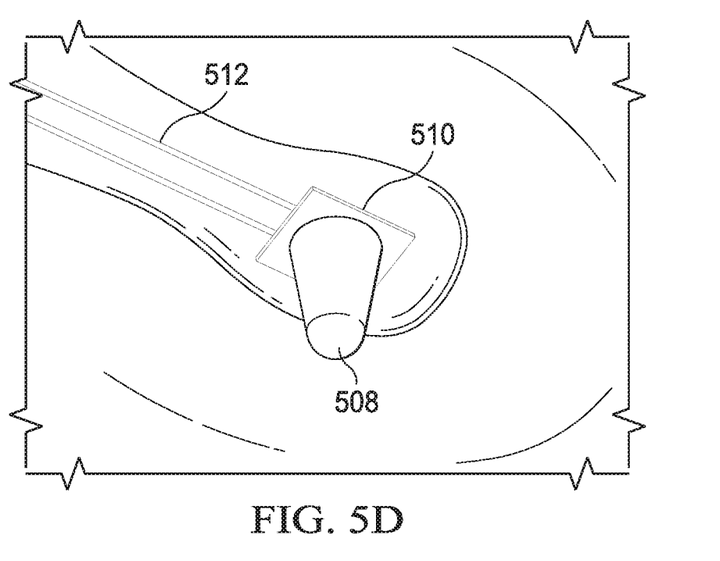

FIG. 5D depicts a magnified view of direction control mechanism 508 in accordance with an illustrative embodiment. As is illustrated, direction control mechanism 508 is coupled to sensor 510 in accordance with an illustrative embodiment. In this example, sensor 510 is illustrated as a foil that includes one strain gauge (piezo-resistive) sensor. Again, while sensor 510 of FIG. 5D illustrates one strain gauge, the illustrative embodiments recognize that any number sensors may be utilized so as to provide higher accuracies in detecting movement by the user's tongue. In FIG. 5D, coupling 512 is shown to have two wires. This is because, in this example, sensor 510 is utilizing one strain gauge and each strain gauge requires two wires. Thus, the two wires are only one example and sensor 510 may comprise any number of sensors so as to provide higher accuracies in detecting movement by the user's tongue.

Figure 6:
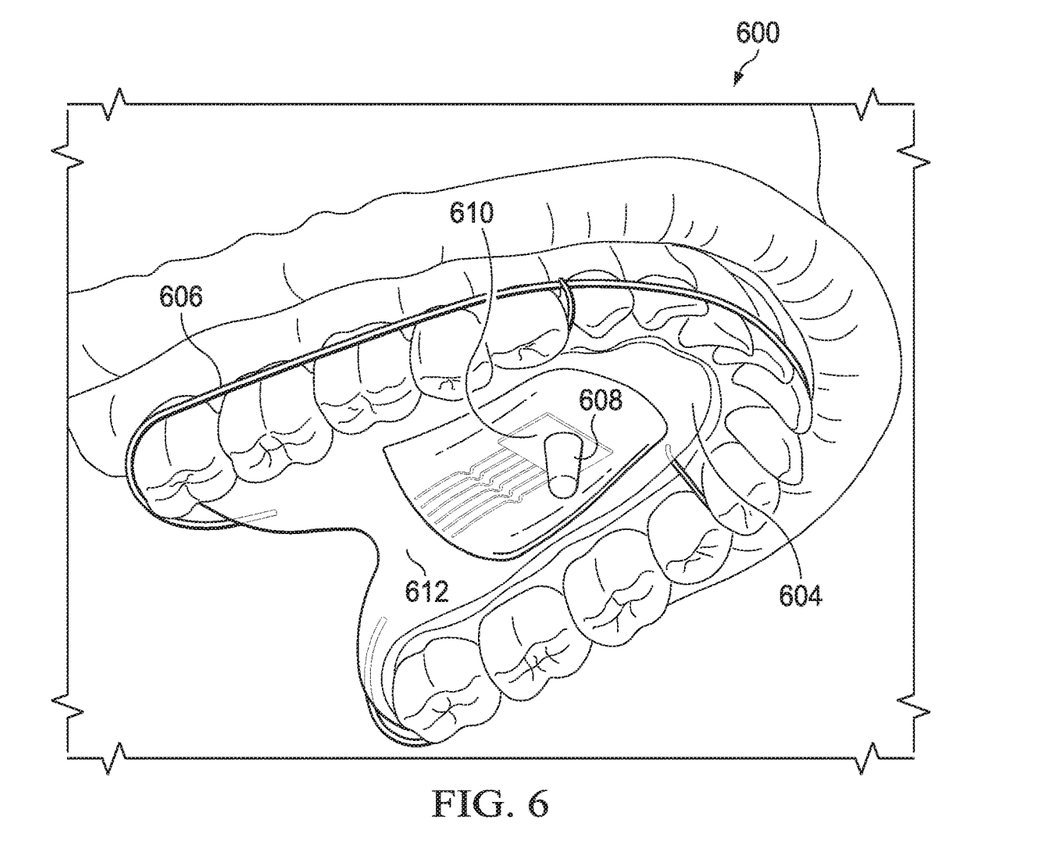
FIG. 6 depict one example of an intraoral control mechanism would fit within a user's mouth in accordance with an illustrative embodiment.

FIG. 6 depict one example of an intraoral control mechanism, such as intraoral control mechanism 300 of FIG. 3 and intraoral control mechanism 400 of FIG. 4, would fit within a user's mouth in accordance with an illustrative embodiment. As is illustrated, intraoral control mechanism 600 comprises molded plastic center section 604 affixed to wires 606 that wrap around the user's upper teeth and hold dental retainer 502 in the user's mouth. Molded plastic center section 604 comprises at least direction control mechanism 608 and sensor 610. Sensor 610 is then coupled to other components, i.e. the amplifier, analog-to-digital converter, RF microcontroller, and antenna, which may be comprised within the molded plastic center section 604 or affixed to wires 606, via coupling 612. It should also be noted that all devices, i.e. sensor 610, coupling 612, or the like, are insulated in accordance with the illustrative embodiments so as to protect the user.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the Python programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 7:
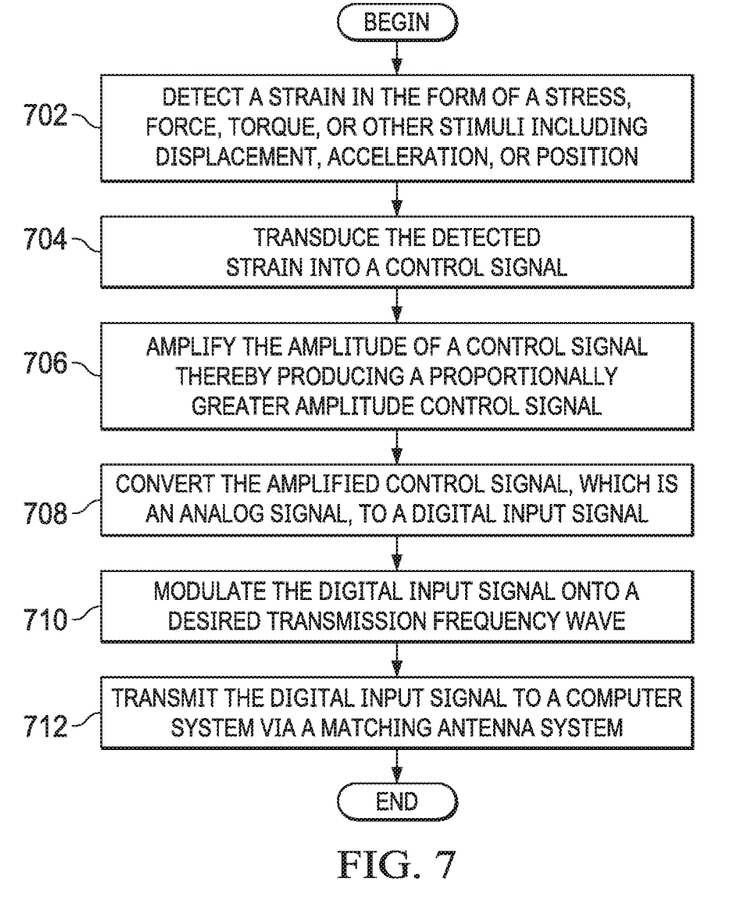
FIG. 7 depicts one exemplary flowchart of the operation performed by an intraoral control mechanism so that a user is able to control the operation of an electronic device in accordance with an illustrative embodiment.

FIG. 7 depicts one exemplary flowchart of the operation performed by an intraoral control mechanism so that a user is able to control operation of an electronic device in accordance with an illustrative embodiment. As the operation begins, a sensor of the intraoral control mechanism detects a strain in the form of a stress, force, torque, or other stimuli including displacement, acceleration, or position (step 702). The strain detected by the sensor comes from a control mechanism, which may take the form of kinematic, spreading, breakup, recoiling, bouncing, or the like feature which, when touched by a tongue of a user. Utilizing the detected strain, the sensor transduces the detected strain into a control signal (step 704) such as on, off, select, forward, backward, left, right, up, down, etc.

An amplifier of the intraoral control mechanism uses electric power from a power supply to amplify the amplitude of the control signal thereby producing a proportionally greater amplitude control signal, i.e. an amplified control signal (step 706). An analog-to-digital converter of the intraoral control mechanism converts the amplified control signal, which is an analog signal, to a digital input signal (step 708). A radio frequency (RF) microcontroller of the intraoral control mechanism then modulates the digital input signal onto a desired transmission frequency wave (step 710). The RF microcontroller then transmits the digital input signal to a computer system via a matching antenna system (step 712). The computer system then interprets the digital input signal by means of pre-trained classifiers and other software into a digital control signal, such that the computer system executes the digital control signal on the computer system itself and performs the desired operation or the computer system transmits the digital control signal to an electronic device control mechanism of the electronic device thereby causing the electronic device in which the electronic device control mechanism is comprised to operate an electronic device in a manner as indicated by the digital control signal. The operation ends thereafter and may or may not be stored for analysis.

Figure 8:
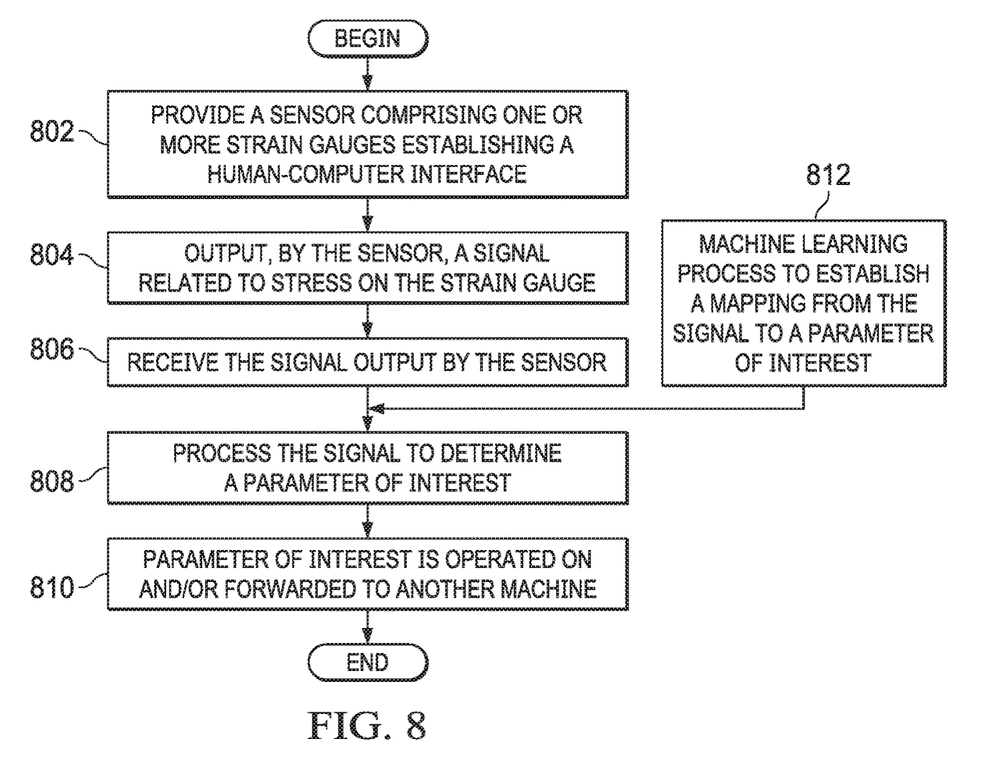
FIG. 8 depicts one exemplary flowchart of the operation performed by a computer system receiving a digital input signal from an intraoral control mechanism to control operation of an electronic device in accordance with an illustrative embodiment.

FIG. 8 depicts one exemplary flowchart of the operation performed by a computer system receiving a digital input signal from an intraoral control mechanism to control operation of an electronic device in accordance with an illustrative embodiment. According to one or more embodiments of the present invention, a the intraoral control system includes providing a sensor comprising one or more strain gauges establishing a human-computer interface (step 802) that outputs, by the sensor, a signal related to stress on the strain gauge (step 804). A receiver receives the signal output by the sensor (step 806) and processes the signal to determining a parameter of interest (step 808). According to one or more embodiments of the present invention, the parameter of interest is a characterization of a movement, which can assist with mobility, transportation, communication, activities of daily living, and performance of job related activities. It should be understood that the parameters described herein are exemplary, and that one of ordinary skill in the art would recognize that additional parameters can be mapped to the signal output by the sensor. In accordance with the illustrative embodiment, the parameter of interest is then operated on and or forwarded to another machine (step 810).

According to one or more embodiments of the present invention, a machine learning process (step 812) establishes, for the sensor, a mapping from the signal (e.g., a waveform signal) to a parameter of interest (step 808). The mapping is used in processing the signal at step 808. For example, the output of the sensor can be instrumented to determine that a given waveform corresponds to certain movement.

According to one or more embodiments of the present invention, the machine learning process at step 812 and the signal processing at step 808 are adapted to mobility devices such as wheelchairs, walkers, and crutches that help people who are unable to walk on their own.

According to an embodiment of the present invention, for a characterization of a movement, the machine learning at step 812 includes a training session. The machine learning process at step 812 further includes an estimation of a piece-wise linear regression model from the strain measurements and movement measurements. Given the piece-wise linear regression model (i.e., step 812), the signal processing at step 808 inputs the signal into the model to predict a parameter of interest, in this exemplary case. According to an embodiment of the present invention, the signal processing at step 808 comprises grouping/clustering the received strain signals (see step 806) into movements. The signal processing at step 808 includes recording strain signals over time (e.g., at different visits to a physician or technician, when in wireless communications range of a receiver, etc.), wherein a strain is observed for one or more of the movement, and is compared over time.

Given the strain measurements and the known movements, the machine learning at step 812 includes grouping the strain measurements corresponding to the known movement actions, applying dynamic time warping (DTW), and identifying idioms. DTW is a method of measuring the similarity between two temporal sequences that vary in speed. In one or more embodiments of the present invention, a DTW method is applied to compensate for variability (e.g., different subjects doing things at different speeds), wherein the DTW outputs a set of aligned strain measurements. The machine learning at step 812 further includes generating a classifier (e.g., k-nearest neighbors, support vector machines (SVM), neural networks, etc.) trained using the strain measurements mapped to character and gesture labels. According to an embodiment of the present invention, the signal processing at step 808 receives signals from the sensor and predicting characters and/or gestures from the received signals using the classifier.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide mechanisms for intraoral control mechanism that allows a user to control the operation of an electronic device. The illustrative embodiments provide a soft, biologically inspired eccentrically shaped 'controller' that may be constructed in shapes that are easily manipulated with a body part (e.g. tongue) but otherwise stay out of the way during other uses (e.g. chewing, swallowing, talking). The movements of this controller by the human user is transduced by a sensor into a digital signal that is deconvolved by trained classifiers into 'control' operations, such as on, off, select, forward, backward, left, right, up, etc.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system, comprising at least one processor and at least one memory, wherein the at least one memory comprises instructions that are executed by the at least one processor to configure the at least one processor to implement an intraoral control mechanism that allows a user to control an operation of a computer system or an electronic device in accordance with an illustrative embodiment, the method comprising:

generating a machine learning classifier trained using strain measurements mapped to character and gesture labels;

receiving, from an intraoral control mechanism, a digital input signal, wherein the digital input control signal is received from the intraoral control mechanism through the intraoral control mechanism performing the following:
   detecting, by a sensor of the intraoral control mechanism, a strain cause by a tongue of a user moving a control mechanism away from a fixed position, wherein the intraoral control mechanism is comprised within a dental retainer worn by the user, wherein the dental retainer comprises a molded plastic center section that affixes to the hard palate in the user's mouth, and wherein the molded plastic center section comprises at least the control mechanism and the sensor;
   transducing, by the sensor, the detected strain into a control signal;
   amplifying, by an amplifier of the intraoral control mechanism, an amplitude of the control signal thereby producing an amplified control signal;
   converting, by an analog-to-digital converter of the intraoral control mechanism, the amplified control signal to a digital input signal;
   modulating, by a radio frequency (RF) microcontroller of the intraoral control mechanism, the digital input signal onto a transmission frequency wave;
   transmitting, by the RF microcontroller, the digital input signal to the computer system;
predicting characters or gestures from the digital input signal using the machine learning classifier;
performing, by the computer system, an operation based on the predicted characters or gestures; and
saving the digital input signal for analysis and characterization of the user.

2. The method of claim 1, wherein the amplifier, the analog-to-digital converter, the microcontroller, and the antenna are comprised within the molded plastic center section.

3. The method of claim 1, wherein the amplifier, the analog-to-digital converter, the microcontroller, and the antenna are comprised within wires attached to the molded plastic center section, the wires wrapping around the user's upper teeth and holding the dental retainer in the user's mouth.

4. The method of claim 1, wherein the control mechanism has 360 degrees of motion and an up motion followed by a down motion.

5. The method of claim 1, wherein the sensor is selected from the group consisting of a metal structure, a piezo-resistive structure, or a piezoelectric structure.

6. The method of claim 1, wherein the strain is selected from the group consisting of a stress, a force, a torque, a displacement, an acceleration, or a position.

7. The method of claim 1, wherein the control mechanism is a projection on a molded plastic center section of a dental retainer and wherein the projection is selected from the group consisting of a kinematic projection, spreading projection, breakup projection, recoiling projection, or bouncing projection.

8. The method of claim 1, wherein the control signal indicates an operation for the electronic device and wherein the operation is selected from the group consisting of on, off, select, forward, backward, left, right, up, down, or any other arbitrarily defined operation.

9. An apparatus comprising:
at least one processor; and
at least one memory coupled to the at least one processor, wherein the at least one memory comprises instructions which, when executed by the at least one processor, cause the at least one processor for allowing a user to control an operation of a computer system or an electronic device in accordance with an illustrative embodiment, and further cause the at least one processor to:
receive, from an intraoral control mechanism, a digital input signal, wherein the digital input control signal is received from the intraoral control mechanism through the intraoral control mechanism performing the following:
   detecting, by a sensor of the intraoral control mechanism, a strain cause by a tongue of a user moving a control mechanism away from a fixed position, wherein the intraoral control mechanism is comprised within a dental retainer worn by the user, wherein the dental retainer comprises a molded plastic center section that affixes to the hard palate in the user's mouth, and wherein the molded plastic center section comprises at least the control mechanism and the sensor;
   transducing, by the sensor, the detected strain into a control signal;
   amplifying, by an amplifier of the intraoral control mechanism, an amplitude of the control signal thereby producing an amplified control signal;
   converting, by an analog-to-digital converter of the intraoral control mechanism, the amplified control signal to a digital input signal;
   modulating, by a radio frequency (RF) microcontroller of the intraoral control mechanism, the digital input signal onto a transmission frequency wave; and
   transmitting, by the RF microcontroller, the digital input signal to the computer system;
predict characters or gestures from the digital input signal using the machine learning classifier;
either:
perform, by the computer system an operation based on the predicted characters or gestures; and
save the digital input signals for analysis and characterization of the user.

10. The method of claim 1, further comprising grouping strain measurements corresponding to known movement actions, applying dynamic time warping, and identifying idioms.

11. The method of claim 1, wherein the machine learning classifier comprises a piece-wise linear regression model.

12. The method of claim 1, wherein saving the digital input signals comprises recording strain signals over time at different visits to a physician or technician.

13. The method of claim 1, wherein analysis and characterization of the user comprise characterizing health states related to chewing, swallowing, coughing, bruxism, or temporomandibular joint disorders.

14. The apparatus of claim 9, wherein the control mechanism has 360 degrees of motion and an up motion followed by a down motion.

15. The apparatus of claim 14, wherein the amplifier, the analog-to-digital converter, the microcontroller, and the antenna are comprised within the molded plastic center section.

16. The apparatus of claim 14, wherein the amplifier, the analog-to-digital converter, the microcontroller, and the antenna are comprised within wires attached to the molded plastic center section, the wires wrapping around the user's upper teeth and holding the dental retainer in the user's mouth.

17. The apparatus of claim 14, wherein the sensor is selected from the group consisting of a metal structure, a piezo-resistive structure, or a piezoelectric structure.

18. The apparatus of claim 14, wherein the strain is selected from the group consisting of a stress, a force, a torque, a displacement, an acceleration, or a position.

19. The apparatus of claim 14, wherein the control mechanism is a projection on a molded plastic center section of a dental retainer and wherein the projection is selected from the group consisting of a kinematic projection, spreading projection, breakup projection, recoiling projection, or bouncing projection.

20. A computer program product comprising a computer readable storage medium having a computer readable program for allowing a user to control an operation of a computer system or an electronic device stored therein, wherein the computer readable program, when executed on a data processing system, causes the data processing system to:
  receive, from an intraoral control mechanism, a digital input signal, wherein the digital input control signal is received from the intraoral control mechanism through the intraoral control mechanism:
    detecting, by a sensor of the intraoral control mechanism, a strain cause by a tongue of a user moving a control mechanism away from a fixed position, wherein the control mechanism is comprised within a dental retainer worn by the user, wherein the dental retainer comprises a molded plastic center section that affixes to the hard palate in the user's mouth, and wherein the molded plastic center section comprises at least the control mechanism and the sensor;
  transducing, by the sensor, the detected strain into a control signal;
  amplifying, by an amplifier of the intraoral control mechanism, an amplitude of the control signal thereby producing an amplified control signal;
  converting, by an analog-to-digital converter of the intraoral control mechanism, the amplified control signal to a digital input signal;
  modulating, by a radio frequency (RF) microcontroller of the intraoral control mechanism, the digital input signal onto a transmission frequency wave; and
  transmitting, by the RF microcontroller, the digital input signal to the computer system; and
predict characters or gestures from the digital input signal using the machine learning classifier;
perform, by the computer system an operation based on the predicted characters or gestures; and
save the digital input signals for analysis and characterization of the user.

* * * * *